US010004657B2

(12) United States Patent
Martin et al.

(10) Patent No.: US 10,004,657 B2
(45) Date of Patent: Jun. 26, 2018

(54) METHOD OF BRAIN ACTIVATION

(75) Inventors: Ruth E. Martin, London (CA); Peter Soros, Columbia, SC (US)

(73) Assignee: THE UNIVERSITY OF WESTERN ONTARIO, London (CA)

( * ) Notice: Subject to any disclaimer, the term of this patent is extended or adjusted under 35 U.S.C. 154(b) by 1192 days.

(21) Appl. No.: 12/322,562

(22) Filed: Feb. 4, 2009

(65) Prior Publication Data

US 2010/0010400 A1 Jan. 14, 2010

Related U.S. Application Data

(60) Provisional application No. 61/006,973, filed on Feb. 8, 2008.

(51) Int. Cl.
| | |
|---|---|
| *A61H 9/00* | (2006.01) |
| *A61B 5/055* | (2006.01) |
| *A61B 5/00* | (2006.01) |
| *A61H 13/00* | (2006.01) |

(52) U.S. Cl.
CPC ........... *A61H 9/0071* (2013.01); *A61B 5/055* (2013.01); *A61B 5/4076* (2013.01); *A61B 5/4205* (2013.01); *A61H 9/00* (2013.01); *A61H 9/005* (2013.01); *A61H 9/0007* (2013.01); *A61H 13/00* (2013.01)

(58) Field of Classification Search
CPC ........ A61H 9/00; A61H 9/0007; A61H 9/005; A61H 9/0071; A61H 13/00; A61H 13/005
USPC ....... 601/154, 155, 160, 161, 162, 164, 165; 600/23, 24; 604/19, 23, 24, 25, 26, 27; 606/191, 196; 128/200.14, 200.24
See application file for complete search history.

(56) References Cited

U.S. PATENT DOCUMENTS

| | | | |
|---|---|---|---|
| 3,747,595 A * | 7/1973 | Grossan | 601/160 |
| 3,853,105 A | 12/1974 | Kenagy | |
| 4,071,026 A | 1/1978 | Bevins | |
| 4,170,230 A | 10/1979 | Nelson | |
| 4,572,177 A | 3/1986 | Tiep et al. | |
| 4,576,190 A | 3/1986 | Youssef | |
| 4,676,774 A | 6/1987 | Semm et al. | |
| 4,679,551 A | 7/1987 | Anthony | |
| 4,773,898 A | 9/1988 | Begouen | |
| 4,790,305 A | 12/1988 | Zoltan et al. | |
| 4,996,990 A | 3/1991 | Hideshima | |
| 5,062,795 A * | 11/1991 | Woog | 433/80 |

(Continued)

FOREIGN PATENT DOCUMENTS

| | | |
|---|---|---|
| CA | 2064882 | 2/1991 |
| CA | 2203257 | 5/1996 |

(Continued)

OTHER PUBLICATIONS

Yoshida K, Maezawa H, Nagamine T, Fukuyama H, Murakami K, Iizuka T. Somatosensory evoked magnetic fields to air-puff stimulation on the soft palate. Nov. 25, 2005. Neuroscience Research. 55. pp. 116-122.*

(Continued)

*Primary Examiner* — Colin W Stuart
(74) *Attorney, Agent, or Firm* — Brinks Gilson & Lione (57) ABSTRACT

A method of activating the brain of a subject by delivering at least one gas pulse or fluid pulse of a predetermined amplitude and duration to a predetermined area or areas on the subject's body.

9 Claims, 4 Drawing Sheets
(3 of 4 Drawing Sheet(s) Filed in Color)

(56) References Cited

U.S. PATENT DOCUMENTS

| | | | |
|---|---|---|---|
| 5,066,502 A | 11/1991 | Eales | |
| 5,085,634 A | 2/1992 | Lackney | |
| 5,143,087 A | 9/1992 | Yarkony | |
| 5,147,298 A | 9/1992 | Turner et al. | |
| 5,176,151 A | 1/1993 | Harding | |
| 5,213,553 A | 5/1993 | Light | |
| 5,377,688 A | 1/1995 | Aviv et al. | |
| 5,515,860 A | 5/1996 | Aviv et al. | |
| H1557 H * | 7/1996 | Joubert et al. | 600/590 |
| 5,566,645 A | 10/1996 | Cole | |
| 5,725,564 A | 3/1998 | Freed et al. | |
| 5,735,772 A | 4/1998 | Schiavoni | |
| 5,826,570 A | 10/1998 | Goodman et al. | |
| 5,855,908 A | 1/1999 | Stanley et al. | |
| 5,884,625 A | 3/1999 | Hart | |
| 5,891,185 A | 4/1999 | Freed et al. | |
| 5,897,492 A | 4/1999 | Feller et al. | |
| 5,950,624 A | 9/1999 | Hart | |
| 5,954,673 A | 9/1999 | Stachlin et al. | |
| 5,970,978 A * | 10/1999 | Aviv et al. | 128/207.14 |
| 5,993,413 A | 11/1999 | Aaltonen et al. | |
| 6,036,655 A | 3/2000 | Aviv et al. | |
| D422,694 S | 4/2000 | Hill | |
| 6,104,958 A | 8/2000 | Freed et al. | |
| 6,264,058 B1 | 7/2001 | Porter et al. | |
| 6,295,988 B1 | 10/2001 | Sue | |
| 6,299,592 B1 | 10/2001 | Zander | |
| 6,355,003 B1 | 3/2002 | Aviv et al. | |
| 6,454,788 B1 | 9/2002 | Ashton | |
| 6,484,053 B2 | 11/2002 | Leelamanit | |
| 6,591,140 B2 | 7/2003 | Strome et al. | |
| 6,607,549 B2 | 8/2003 | Huang | |
| 6,805,127 B1 | 10/2004 | Karasic | |
| 6,916,287 B2 * | 7/2005 | Dematteis et al. | 600/184 |
| 6,935,857 B1 | 8/2005 | Farrell | |
| 6,960,183 B2 | 11/2005 | Nicolette | |
| 7,021,930 B2 | 4/2006 | Schemmer et al. | |
| 7,039,468 B2 | 5/2006 | Freed et al. | |
| 7,083,548 B1 | 8/2006 | Moore et al. | |
| 7,118,377 B2 | 10/2006 | Inoue et al. | |
| 7,147,468 B2 | 12/2006 | Snyder et al. | |
| 7,238,145 B2 | 7/2007 | Robbins et al. | |
| 7,239,918 B2 | 7/2007 | Strother et al. | |
| 7,273,327 B2 | 9/2007 | Hohlbein et al. | |
| 7,477,947 B2 | 1/2009 | Pines et al. | |
| 7,660,636 B2 | 2/2010 | Castel et al. | |
| 7,694,674 B2 * | 4/2010 | Crome et al. | 128/202.26 |
| 7,935,065 B2 * | 5/2011 | Martin et al. | 600/590 |
| 2001/0050086 A1 * | 12/2001 | Addington et al. | 128/898 |
| 2002/0082544 A1 | 6/2002 | Thrash | |
| 2003/0015198 A1 | 1/2003 | Heeke et al. | |
| 2003/0104342 A1 | 6/2003 | Lynch et al. | |
| 2004/0000054 A1 | 1/2004 | Sommer | |
| 2004/0138585 A1 | 7/2004 | Dematteis et al. | |
| 2005/0222535 A1 | 10/2005 | Uesugi et al. | |
| 2006/0110710 A1 | 5/2006 | Schemmer et al. | |
| 2006/0210480 A1 | 9/2006 | Hamdy | |
| 2006/0235352 A1 | 10/2006 | Dziewas et al. | |
| 2006/0282010 A1 * | 12/2006 | Martin et al. | 600/560 |
| 2007/0156182 A1 | 7/2007 | Castel et al. | |
| 2008/0009810 A1 | 1/2008 | Hamdy | |
| 2008/0018611 A1 | 1/2008 | Serban et al. | |
| 2008/0077192 A1 | 3/2008 | Harry et al. | |
| 2008/0147142 A1 | 6/2008 | Testerman et al. | |
| 2008/0251597 A1 | 10/2008 | Pearson | |
| 2008/0269837 A1 | 10/2008 | Ludlow et al. | |
| 2008/0269856 A1 | 10/2008 | Cross et al. | |
| 2008/0269857 A1 | 10/2008 | Cross et al. | |
| 2008/0269858 A1 | 10/2008 | Cross et al. | |
| 2008/0269859 A1 | 10/2008 | Cross et al. | |
| 2008/0269860 A1 | 10/2008 | Cross et al. | |
| 2008/0269861 A1 | 10/2008 | Cross et al. | |
| 2009/0048645 A1 | 2/2009 | Philipp et al. | |
| 2009/0048647 A1 | 2/2009 | Tingey | |
| 2009/0054980 A1 | 2/2009 | Ludlow et al. | |
| 2009/0120446 A1 | 5/2009 | Vaska et al. | |
| 2009/0120447 A1 | 5/2009 | Vaska et al. | |
| 2009/0123886 A1 | 5/2009 | Vaska | |
| 2009/0137859 A1 | 5/2009 | Belafsky et al. | |
| 2009/0249571 A1 | 10/2009 | Rohrig | |
| 2009/0259310 A1 | 10/2009 | Blom | |
| 2009/0286237 A1 | 11/2009 | Fitzgerald et al. | |
| 2009/0306626 A1 | 12/2009 | Sinha et al. | |
| 2009/0306741 A1 | 12/2009 | Hogle et al. | |
| 2010/0016908 A1 | 1/2010 | Martin et al. | |
| 2010/0055233 A1 | 3/2010 | Macinnis et al. | |
| 2010/0121224 A1 | 5/2010 | Toyota et al. | |

FOREIGN PATENT DOCUMENTS

| | | |
|---|---|---|
| EP | 1 314 430 B1 | 9/2007 |
| JP | 11309186 A | 11/1999 |
| WO | WO 90/10470 A1 | 9/1990 |
| WO | WO 02/38012 A2 | 5/2002 |
| WO | WO 2003/061453 A2 | 7/2003 |
| WO | WO 2004/028433 A2 | 4/2004 |
| WO | WO 2004/028433 A3 | 4/2004 |
| WO | WO 2004/069076 A2 | 8/2004 |
| WO | WO 2004/075743 A1 | 9/2004 |
| WO | WO 2005/070316 A1 | 8/2005 |
| WO | WO 2005/102458 A2 | 11/2005 |
| WO | WO 2005/122877 A1 | 12/2005 |
| WO | WO 2006/024825 A1 | 3/2006 |
| WO | WO 2006/083217 A1 | 8/2006 |
| WO | WO 2006/106327 A1 | 10/2006 |
| WO | WO 2006/108066 A2 | 10/2006 |
| WO | WO 2006/116843 A1 | 11/2006 |
| WO | WO 2006/108066 A3 | 12/2006 |
| WO | WO 2007/005582 A1 | 1/2007 |
| WO | WO 2007/021468 A2 | 2/2007 |
| WO | WO 2007/021468 A3 | 2/2007 |
| WO | WO 2007/022034 A2 | 2/2007 |
| WO | WO 2007/081764 A2 | 7/2007 |
| WO | WO 2007/081764 A3 | 7/2007 |
| WO | WO 2007/123746 A2 | 11/2007 |
| WO | WO 2007/123746 A3 | 11/2007 |
| WO | WO 2008/076646 A1 | 6/2008 |
| WO | WO 2009/127947 A2 | 10/2009 |

OTHER PUBLICATIONS

Office Action in U.S. Appl. No. 11/411,241, dated Nov. 13, 2009, 12 pgs.

Office Action in Chinese Application No. 200680014928.9, dated Mar. 6, 2009, 5 pgs.

Office Action in Chinese Application No. 200680014928.9, dated Nov. 27, 2009, 6 pgs.

International Search Report in PCT Application No. PCT/CA2006/000650, dated Sep. 6, 2006, 2 pgs.

International Search Report in PCT Application No. PCT/IB2009/005252, dated Oct. 7, 2006, 5 pgs.

Supplementary EPO Search Report in EP Application No. 06721849.5, dated Nov. 24, 2009, 11 pgs.

Gross, Roxann D. et al., "Lung Volume Effects on Pharyngeal Swallowing Physiology", *J. Appl. Physiol*, vol. 95, 2003, pp. 2211-2217.

Hiraba, Hisao et al., "Increased Secretion of Salivary Glands Produced by Facial Vibrotactile", *Somatosensory and Motor Research*, vol. 25, 2008, pp. 222-229.

Jafari, Samah et al., "Sensory Regulation of Swallowing and Airway Protection: A Role for the Internal Superior Layngeal Nerve in Humans", *J. Physiol*, vol. 550, No. 1, 2003. pp. 287-304.

Logermann, Jeri A., " The Effects of VitalStim on Clinical Research Thinking in Dysphagia", *Dysphagia*, No. 22, 2007, pp. 11-12.

Lowell, Soren et al., "Sensory Stimulation Activates Both Motor and Sensory Components of the Swallow System", *NeuroImage*, vol. 42, 2008, pp. 295-295.

Lowell, Soren et al., "The Effects of Sensory Stimulation on Urge and Frequency of Swallowing", *PPT Presentation made at the 2008 meeting of the Dysphagia Research Society*, National Institutes of Heath, 2008, 14 pgs.

(56) References Cited

OTHER PUBLICATIONS

Brochure, Pentax, ENT Scopes, 2005, 2 pgs.
Sörös, P. et al., "Functional MRI of Oropharyngeal Air-Pulse Stimulation", *Neuroscience*, vol. 53, 2008, pp. 1300-1308.
Theurer, Julie et al., "The Effects of Oropharyngeal Air-Pulse Stimulation on Swallowing in Healthy Older Adults", *Dysphagia*, 2009, 12 pgs.
Program of the 103rd Meeting of the Acoustical Society of America, *J. Acoust. Am.*, 1982, Suppl. 1, vol. 71 pp. S1-S113.
Ali, Galib N. et al., "Influence of Cold Stimulation on the Normal Pharyngeal Swallow Response", *Dysphagia*, 1996, vol. 11, pp. 2-8.
Aviv, Jonathan E. et al., "Air Pulse Quantification of Supraglottic and Pharyngeal Sensation: A New Technique", *Ann Otol Rhinol Laryngol*, 1993, vol. 102, pp. 777-780.
Aviv, Jonathan E. et al., "Clinical assessment of Pharyngolaryngeal Sensitivity", *The American Journal of Medicine*, 2000, vol. 108 (4A), pp. 68S-72S.
Aviv, Jonathan E. et al., "Effects of Aging on Sensitivity of the Pharyngeal and Supraglottic Areas", *The American Journal of Medicine*, 1997, vol. 103 (5A), pp. 74S-76S.
Aviv, Jonathan E. et al., "Laryngopharyngeal Sensory Deficts in Patients with Laryngopharyngeal Reflux and Dysohagia", *Ann Otol Rhinol Laryngol*, 2000, vol. 109, pp. 1000-1006.
Aviv, Jonathan E. et al., "Laryngopharyngeal Sensory Discrimination Testing and the Laryngeal Adductor Reflex", *Ann Otol Rhinol Laryngol*, 1999, vol. 108, pp. 725-730.
Aviv, Jonathan E. et al., "Silent Laryngopharyngeal Sensory Deficits After Stroke", *Ann Otol Rhinol Laryngol*, 1997, vol. 106, pp. 87-93.
Aviv, Jonathan E. et al., "Supraglottic and Pharyngeal sensory Abnormalities in Stroke patients with Dysphagia", *Ann Otol Rhinol Laryngol*, 1996, vol. 105, pp. 92-97.
Aviv, Jonathan E. et al., "Surface sensibility of the floor of the mouth and tongue in healthy controls and in radiated patients", *Annual Meeting of the American Academy of Otolaryngology—Head and Neck Surgery*, Kansas City, MO., 1991, pp. 418-423.
Balzamo, E. et al., "Short-latency components of evokes potentials to median nerve stimulation recorded by intracerebral electrodes in the human pre- and postcentral areas", *Clinical Neurophysiology*, 2004, vol. 115, pp. 1616-1623.
Barberi, Enzo A. et al., "A Transmit-Only/Receive-Only (TORO) RF System for High-Field MRI/MRS Applications", *Magnetic Resonance in Medicine*, 2000, Vil. 43, pp. 284-289.
Beckmann, Christian F. et al., "Probabilistic Independent Component Analysis for Functional Magnetic Resonance Imaging", *IEEE Transactions on medical Imaging*, 2004, vol. 23, No. 2. pp. 137-152.
Bessho, H. et al., "Localization of Palatal Area in Human Somatosensory Cortex", *J Dent Res*, 2007, vol. 86, No. 3, pp. 265-270.
Boliek, C. A. et al., "Effect of age on salivary flow obtained under feeding and non-feeding conditions", *Journal of Oral Rehabilitation*, 2007, vol. 34, pp. 433-441.
Bourdiol, P. et al., "Establishing a reliable protocol to measure tongue sensation", *Journal of Oral Rehabilitation*, 2004, vol. 31, pp. 445-452.
Bove, Mogens et al., "Thermal Oral-Pharyngeal Stimulation and Elicitation of Swallowing", *Acta Otolaryngol (Stochk)*, 1998, vol. 118. pp. 728-731.
Broekhuusen M. L. et al., "Factors Influencing jaw Position Sense in Man", *Archs oral Biol.*, 1983, vol. 28, No. 5, pp. 387-391.
Calhoun, Karen K. et al., "Age-Related Changes in Oral Sensation", *Laryngoscope*, 1992, vol. 102, pp. 109-116.
Capra, Norman F., "Mechanism of Oral Sensation", *Dysphagia*, 1995, vol. 10, pp. 235-247.
Chamberlain, Cheryl K. et al., "Intra-oral tactile sensation and aging in a community-based population", *Aging Clin Exp Res*, 2006, vol. 19, No. 2, pp. 85-90.
Cook, I. J. et al., "Influence of aging on oral-pharyngeal bolus transit and clearance during swallowing: scintigraphic study", *The American Physiological Society*, 1994, pp. G972-G977.

Craig, A. D. et al., "Thermosensory activation of insular cortex", 2000, *Nature Neuroscience*, vol. 3, No. 2, pp. 184-190.
Dale et al. "Cortical Surface-Based Analysis", *NeuroImage*, 1999, vol. 9, pp. 179-194.
Darian-Smith, I. et al., "Somatic Sensory Cortical Projection Areas Excited by Tactile Stimulation of the Cat: A Triple Representation", *J. Physiol.*, 1966, vol. 182. pp. 671-689.
Dawes, C., "Circadian Rhythms in Human Salivary Flo Rate and Composition", *J. Physiol.*, 1972, vol. 220. pp. 529-545.
Dawes, C. et al., "Circadian Rhythms in the Flow Rate and Proportional Contribution of Parotid to Whole Saliva Volume In Man", *Archs oral Biol.*, 1973, vol. 18. pp. 1145-1153.
Ding, Ruiying et al., "The Effects of taste and Consistency on Swallow Physiology in Younger and Older Healthy Individuals: A Surface Electromyographic Study", *Journal of Speech, Language, and Hearing Research*, 2003, vol. 46, pp. 977-989.
Disbrow, Elizabeth A. et al., "Ipsilateral Representation of Oral Structures in Human Anterior Parietal Somatosensory Cortex and Integration of Inputs Across the Midline", *The Journal of Comparative Neurology*, 2003, vol. 467, pp. 487-495.
Do, David H. et al., "Resolving Subjects and Measuring Observer/Subject Distances with a Thermal Tactile Imager", IEEE, 30th Annual International IEEE EMBS Conference, Vancouver, Canada, 2008, pp. 4302-4305.
Doty, Robert W., "Influence of Stimulus pattern on Reflex Deglutition", *Dept. Of Physiology, The University of Chicago*, 1951, vol. 166, pp. 142-158.
Dum, Richard R. et al., "Motor areas in the frontal lobe of the primate", *Physiology and Behavior*, 2002, vol. 77, pp. 677-682.
Ettlin, D. A. et al., "Cortical Activation Resulting from Painless Vibrotactile Dental Stimulation Measured by Functional Magnetic Resonance Imaging (fMRI)", *J. Dent Res.*. 2004, vol. 83, No. 10. pp. 757-761.
Fabri, Mara et al., "Bulateral Cortical Representation of the Trunk Midline in Human First Somatic Sensory Area", *Human Brain Mapping*, 2005, vol. 25, pp. 287-296.
Ferguson D. B. et al., "Circadian Rhythms in Human Partotid Saliva Flow Rate and Composition", *Archs oral Biol.*, 1973, vol. 18. pp. 1155-1173.
Flynn, Frederick et al., "Anatomy of the insula-functional clinical correlates", *Aphasiology*, 1999, vol. 13, No. 1, pp. 55-78.
Fraser, Chris et al., "Driving Plasticity in Human Adult Motor Cortex is Associated with Improved Motor Function after Brain Injury", *Neuron*, 2002, vol. 34, pp. 831-840.
Fujiu, Masako et al., "Glossopharyngeal evoked potentials in normal subjects following n=mechanical stimulation of the anterior faucial pillar", *Electroencephalography and Clinical Neurophysiology*, 1994, vol. 92, pp. 183-195.
Fukunaga, Akiko et al., "Influences of Aging on Taste Perception and Oral Somatic Sensation", *Journal of Gerontology: Medical Sciences*, 2005, vol. 60A, No. 1, pp. 109-113.
Gemba, Hisae et al., "Influences of emotion upon parotid secretion in human", *Neuroscience Letters*, 1996, vol. 211, pp. 159-162.
Hamdy, Shaheen et al., "Cranial nerve modulation of human cortical swallowing motor pathways", *American Physiological Society*, 1997, pp. G802-G808.
Hamdy, Shaheen et al., "Explaining oropharyngeal dysphagia after unilateral hemispheric stroke", *The Lancet*, 1997, vol. 350, pp. 686-692.
Hamdy, Shaheen et al., "Long-term reorganization of human motor cortex driven by short-term sensory stimulation", *Nature America Inc.*, 1998, vol. 1, No. 1, pp. 64-68.
Hamdy, S. et al., "Modulation of human swallowing behavior by thermal and chemical stimulation in health and after brain injury", *Neurogastroenterology and Motility*, 2003, vol. 15, pp. 69-77.
Hamdy, Shaheen et al., "Recovery of Swallowing After Dysphagic Stroke Relates to Functional Reorganization in the Intact Motor Cortex", *Gastroenterology*, 1998; vol. 115, No. 5, pp. 1104-1112.
Hamdy, Shaheen et al., "The cortical topography of human swallowing musculature in health and disease", *Nature Medicine*, 1996, vol. 2, No. 11, pp. 1217-1224.
Hayashi, H. et al., "Functional Organization of Trigeminal Subnucleus Interpolaris: Nociceptive and Innocuous Afferent

(56) References Cited

OTHER PUBLICATIONS

Inputs, Projections to Thalamus, Cerebellum, and Spinal Cord, and Descending Modulation From Periaqueductal Gray", *The American Physiological Society, Journal of Neurophysiology*, 1984, vol. 51, No. 5, pp. 890-905.

Huang, C.-S. et al., "Input-Output Relationships of the Primary Face Motor Cortex in the Monkey (*Macaca fascicularis*)", *The American Physiological Society, Journal of Neurophysiology*, 1989, vol. 61, No. 2, pp. 350-362.

Iwamura, Yoshiaki et al., "Bilateral Activity and Callosal Connections in the Somatosensory Cortex", *The Neuroscientist*, 2001, vol. 7, No. 5, pp. 419-429.

Iyengar, Soumya et al., "Cortical and Thalamic Connections of the Representations of the Teeth and Tongue on Somatosensory Cortex of New World Monkeys", *The Journal of Comparative Neurology*, 2007, vol. 501, pp. 95-120.

Jacobs, Reinhilde et al., "Oral stereognosis: a review of the literature", *Clin Oral Invest*, 1998, vol. 2, pp. 3-10.

Jafary, Samah et al., "Sensory regulation of swallowing and airway protection: a role for the internal superior laryngeal nerve in humans", *The physiological Society, J Physiol*, 2003, vol. 30, No. 10, pp. 1-18.

Jain, Neeraj et al., "Anatomic Correlates of the face and Oral Cavity Representations in the Somatosensory Cortical Area 3b Monkeys", *The Journal of Comparative Neurology*, 2001, vol. 429, pp. 455-468.

Jaradeh, Safwan, MD, "Neurophysiology of Swallowing in the Aged", *Dysphagia*, 1994, vol. 9, pp. 218-220.

Jean, Andre, "Brain Stem Control of Swallowing: Neuronal Network and Cellular Mechanisms", *The American Physiological Society*, 2001, vol. 81, No. 2, pp. 929-969.

Jean, Andre et al., "Inputs to the swallowing medullary from the peripheral afferent fibers and the swallowing cortical area", *Brain Research*, 1979, vol. 178, pp. 567-572.

Jobin, Vincent et al., "Swallowing function and upper airway sensation in obstructive sleep apnea", *J. Appl. Physiol.*, 2007, vol. 102, pp. 1587-1594.

Kaatzke-McDonald, Monika N., M App Sc et al., "The Effects of Cold, Touch, and Chemical Stimulation of the Anterior Faucial Pillar on Human Swallowing", *Dysphagia*, 1996, vol. 11, pp. 198-206.

Kapila, Yagya V., MD et al., "Relationship Between Swallow Rate and Salivary Flow", *Digestive Diseases and Sciences*, 1984, vol. 29, No. 6, pp. 528-533.

Kern, Mark K. et al., "Cerebral cortical representation of reflexive and volitional swallowing in humans", *American Physiological Society, Am J Physiol Gastrointest Liver Physiol*, 2001, vol. 280, pp. G354-G360.

Kim, Il Soo et al., "Influence of Mastication and Salivation on Swallowing in Stroke Patients", *Arch Phys Med Rehabil*, 2005, vol. 86, pp. 1986-1990.

Kitagawa, Jun-Ichi et al., "Pharyngeal branch of the glossopharyngeal nerve plays a major role in reflex swallowing from the pharynx", *American Physiological Society, Am J Physiol Regulatory Integrative Comp Physiol*, 2002, vol. 282, pp. R1342-R1347.

Kleim, Jeffrey A. et al., "Principles of Experience-Dependent Neural Plasticity: Implications for Rehabilitation After Brain Damage", *Journal of Speech, Language, and Hearing Research*, 2008, vol. 51, pp. S225-S239.

Lagerlöf, F. et al., "The Volume of Saliva in the Mouth Before and After Swallowing", *Univ of Western Ontario*, 2009, vol. 63, No. 5, pp. 618-621.

Lazzara, Gisela de Lama, M.A. et al., "Impact of Thermal Stimulation on the Triggering of the Swallowing Reflex", *Dysphagia*, 1986, vol. 1, p. 73-77.

Lear, C. S. C. et al., "The Frequency of Deglutition in Man", *Arch. oral Biol.*, 1965, vol. 10, pp. 83-99.

Lim, Kil-Byung, MD, PhD et al., "Neuromuscular Electrical and Thermal-Tactile Stimulation for Dysphagia Caused by Stroke: A Randomized Controlled Trial", *J Rehabil Med*, 2009, vol. 41, pp. 174-178.

Lin, L.-D. et al., "Functional Properties of Single Neurons in the Primate Face Primary Somatosensory Cortex. II. Relations With Different Directions of Trained Tongue Protrusion", *The American Physiological Society, Journal of Neurophysiology*, 1994, vol. 71, No. 6, pp. 2391-2400.

Linden, Patricia, M.A. et al. "Bolus Position at Swallow Onset in Normal Adults: Preliminary Observations", *Dysphagia*, 1989, vol. 4, pp. 146-150.

Logemann, Jeri A. et al., "Closure mechanisms of laryngeal vestibule during swallow", *The American Physiological Society, Am. J. Physiol.*, 1992, vol. 262, pp. G338-G344.

Logemann, Jeri et al., "Effects of a Sour Bolus on Oropharyngeal Swallowing Measures in Patients With Neurogenic Dysphagia", *Journal of Speech and Hearing Research*, 1995, vol. 35, pp. 556-563.

Logemann, Jeri A., Ph.D., "Preswallow Sensory Input: Its Potential Importance to Dysphagic Patients and Normal Individuals", *Dysphagia*, 1996, vol. 11, pp. 9-10.

Logemann, Jeri A. et al., "Temporal and Biomechanical Characteristics of Oropharyngeal Swallow in Younger and Older Men", *American Speech Language-Hearing Association, Journal of Speech, Language, and Hearing Research*, 2000, vol. 43, pp. 1264-1274.

Lowell, Soren Y. et al., "Sensory stimulation activates both motor and sensory components of the swallowing system", *NeuroImage*, 2008, vol. 42, pp. 285-295.

Malenfant, Annie et al., "Tactile, thermal and pain sensibility in burned patients with and without chronic pain and paresthesia problems", *International Association for the Study of Pain*, 1998, vol. 77, pp. 241-251.

Manger, Paul R. et al., "Representation of Face and Intra-Oral Structures in Area 3b of Macaque Monkey Somatosensory Cortex", *The Journal of Comparative Nurology*, 1996, vol. 371, pp. 513-521.

Månsson, Ingemar, M.D. et al., "Effects of Surface Anesthesia on Deglutition in Man", *Department of Otorhinolaryngology, University of Gothenburg, Sweden*, 1973-1974, pp. 427-437.

Marik, Paul E., MD, FCCP et al., "Aspiration Pneumonia and Dysphagia in the Elderly", *American College of Chest Physicians, CHEST*, 2003, vol. 124, pp. 328-336.

Martin, Ruth E. et al., "Cerebral Areas Processing Swallowing and Tongue Movement Are Overlapping but Distinct: A Functional Magnetic Resonance Imaging Study", *The American Physiological Society, J Neurophysiol*, 2004, vol. 92, pp. 2428-2443.

Martin, Ruth et al., "Cerebral cortical processing of swallowing in older adults", *Exp Brain Res*, 2007, vol. 176, pp. 12-22.

Martin, Ruth E. et al., "Cerebral Cortical Representation of Automatic and Volitional Swallowing in Humans", *The American Physiological Society, J Neurophysiol*, 2001, vol. 85, pp. 938-950, www.jn.physiology.org.

Martin, Ruth E. et al., "Features of Cortically Evoked Swallowing in the Awake Primate (*Macaca fascicularis*)", *The American Physiological Society, J. Neurophysiol.*, 1999, vol. 82, pp. 1529-1541.

Martin, Ruth E. et al., "Functional Properties of Neurons in the Primate Tongue Primary Motor Cortex During Swallowing", *The American Physiological Society*, 2007, pp. 1516-1530.

Martin, Ruth E., "Neuroplasticity and Swallowing", *Dysphagia*, 2008.

Martin, Ruth E. et al., "The Role of the Cerebral Cortex in Swallowing", *Dysphagia*, 1993, vol. 8, pp. 195-202.

McKee, G. J. et al., "Does age or sex affect pharyngeal swallowing?", *Clinical Otolaryngology*, 1998, vol. 23, pp. 100-106.

Menon, Ravi S., "Postacquisition Suppression of Large-Vessel BOLD Signals in High-Resolution fMRI", *Magnetic Resonance in Medicine*, 2002, vol. 47, pp. 1-9.

Mese, H. et al., "Invited Review—Salivary secretion, taste and hyposalivation", *Journal of Oral Rehabilitation*, 2007, vol. 34, pp. 711-723.

Miller, Arthur J., "Deglutition", *Physiological Reviews*, 1982, vol. 62, No. 1, pp. 129-184.

(56) References Cited

OTHER PUBLICATIONS

Miyamoto, Jun J. et al., "The Representation of the Human Oral Area in the Somatosensory Cortex: a Functional MRI Study", *Cerebral Cortex*, 2006, vol. 16, No. 5, pp. 669-675.
Mizobuchi, Keiko et al., "Single unit responses of human cutaneous mechanoreceptors to air-puff stimulation", *Clinical Neurophysiology*, 2000, vol. 111, pp. 1577-1581.
Mosier, Kristine, DMD, PhD et al., "Cortical Representation of Swallowing in Normal Adults: Functional Implications", *The American Laryngological, Rhinological and Otological Society, Inc., The Laryngoscope*, 1999, vol. 109, pp. 1417-1423.
Mu, Liancai et al., "Sensory Nerve Supply of the Human Oro- and Laryngopharynx: A Preliminary Study", *The anatomical Record*, 2000, vol. 258, pp. 406-420.
Murray, Joseph et al., "The Significance of Accumulated Oropharyngeal Secretions and Swallowing Frequency in Predicting Aspiration", *Dysphagia*, 1996, vol. 11, pp. 99-103.
Nakamura, Akinori et al., "Somatosensory Homunculus as Drawn by MEG", *NeuroImage*, 1998, vol. 7, pp. 377-386, Article No. NI980332.
Navazesh, M. et al., "A Comparison of Whole Mouth Resting and Stimulated Salivary Measurement Procedures", *J Dent Res*, 1982, vol. 61, No. 10, pp. 1158-1162.
Nguyen, Anh Tu et al., "Laryngeal and Velopharyngeal Sensory Impairment in Obstructive Sleep Apnea", *Sleep*, 2005, vol. 28, No. 5, pp. 585-593.
Ootani, Shinji et al., "Convergence of Afferents from the SLN and GPN in Cat Medullary Swallowing Neurons", *Brain Research Bulletin*, 1995, vol. 37, No. 4, pp. 397-404.
Palmer, Jeffrey B., M.D. et al., "Coordination of Mastication and Swallowing", *Dysphagia*, 1992, vol. 7, pp. 187-200.
Pommerenke, W. T., "A Study of the Sensory Areas Eliciting the Swallowing Reflex", *The American Journal of Physiology*, 1927, vol. 81, No. 1, pp. 36-41.
Power, M. et al., "Changes in pharyngeal corticobulbar excitability and swallowing behavior after oral stimulation", *Am J. Physiol Garstrointest Liver Physiol*, 2004, vol. 286 pp. G45-G50.
Power, Macine L., PhD et al., "Evaluating Oral Stimulation as a Treatment for Dysphagia after Stroke", *Dysphagia*, 2006, pp. 49-55.
Robbins, JoAnne et al., "Swallowing After Unilateral Stroke of the Cerebral Cortex Preliminary Experience", *Dysphagia*, 1988, vol. 3, pp. 11-17.
Robbins, JoAnne et al., "Swallowing and Dysphagia Rehabilitation: Translating Principles of Neural Plasticity Into Clinically Oriented Evidence", *American Speech-Language-Hearing Association, Journal of Speech, Language, and Hearing Research*, 2008, vol. 51, pp. S276-S300.
Rosenbek, John C., PhD et al., "Comparing Treatment Intensities of Tactile-Thermal Application", *Dysphagia*, 1998, vol. 13, pp. 1-9.
Rosenbeck, John C. et al., "Effects of Thermal Application on Dysphagia After Stroke", *Journal of Speech and Hearing Research*, 1991, vol. 34, pp. 1257-1268.
Rosenbek, John C., PhD et al., "Thermal Application Reduces the Duration of Stage Transition in Dysphagia after Stroke", *Dysphagia*, 1996, vol. 11, pp. 225-233.
Ruben, J. et al., "Somatotopic Organization of Human Secondary Somatosensory Cortex", *Cerebral Cortex*, 2001, vol. 11, No. 5, pp. 463-473.
Rudney, J. D. et al., "The Prediction of Saliva Swallowing Frequency in Humans From Estimates of Salivary Flow Rate and the Volume of Saliva Swallowed", *Archs oral Biol.*, 1995, vol. 40, No. 6, pp. 507-512.
Schneyer, Leon H. et al., "Rate of Flow of Human Parotid, Sublingual, and Submaxillary Secretions During Sleep", *J. D. Res.*, 1956, vol. 35, No. 1, pp. 109-114.
Sciortino, Kellie Filter, PhD, CCC-SLP et al., "Effects of Mechanical, Cold, Gustatory, and Combined Stimulation to the Human Anterior Faucial Pillars", *Dysphagia*, 2003, vol. 18, pp. 16-26.

Servos, Philip et al., "fMRI evidence for an inverted face representation in human somatosensory cortex", *NeuroReport*, 1999, vol. 10, No. 7, pp. 1393-1395.
Sessle, Barry J. et al., "Cortical mechanisms controlling mastication and swallowing in the awake monkey", *Brain and oral Functions*, Published by Elsevier Science B.V. 1995, pp. 181-189.
Sessle, B. J., "Review Article, Mechanisms of oral somatosensory and motor functions and their clinical correlates", *Journal of Oral Rehabilitation*, 2006, vol. 33, pp. 243-261.
Shaffer, Scott W. et al., "Aging of the Somatosensory System: A translational Perspective", *American Physical Therapy Association*, 2007, vol. 87, No. 2, pp. 193-207.
Shaw, D. W. et al., "Influence of normal aging on oral-pharyngeal and upper esophageal sphincter function during swallowing", *American Physiological Society, Am. J. Physiol.*, 1995, vol. 268, pp. G389-G396.
Ship, Jonathan A., DMD et al., "Xerostomia and the Geriatric Patient", *Journal of American Geriatric Society*, 2002, vol. 50, No. 3, pp. 535-543.
Simon, Sidney A. et al., "The neural mechanisms of gestation: a distributed processing code", *Nature Reviews, Neuroscience*, 2006, vol. 7, pp. 890-901.
Sinclair, William J., "Role of the pharyngeal plexus in initiation of swallowing", *American Journal of Physiology*, 1971, vol. 221, No. 5, pp. 1260-1263.
Smith, Stephen M., "Fast Robust Automated Brain Extraction", *Human Brain Mapping*, 2002, vol. 17, pp. 143-155.
Sonies, Barbara C., Ph.D. et al., "Durational Aspects of the Oral-Pharyngeal Phase of Swallow in Normal Adults", *Dysphagia*, 1988, vol. 3, pp. 1-10.
Sörös, Peter et al., "Clustered functional MRI of overt speech production", *NeuroImage*, 2006, vol. 32, pp. 376-387.
Sörös, P. et al., "Functional MRI of Oropharyngeal Air-Pulse Stimulation", *Neuroscience*, 2008, vol. 153, pp. 1300-1308.
Sörös, Peter et al., "Research article, Functional MRI of working memory and selective attention in vibrotactile frequency discrimination", *BMC Neuroscience*, 2007, vol. 8, No. 48, pp. 1-10.
Stephen, Jennifer R., MSc et al., "Bolus Location at the Initiation of the Pharyngeal Stage of Swallowing in Healthy Older Adults", *Dysphagia*, 2005, vol. 20, pp. 266-272.
Tanji, J. et al., "Submodality Distribution in Sensorimotor Cortex of the Unanesthetized Monkey", *Journal of Neurophysiology*, 1981, vol. 45, No. 3, pp. 467-481.
Taoka, Miki et al., "Representation of the midline trunk, bilateral arms, and shoulders in the monkey postcentral somatosensory cortex", *Exp Brain Res*, 1998, vol. 123, pp. 315-322.
Theurer, Julie A., MCISc et al., "Oropharyngeal Stimulation with Air-Pulse Trains Increases Swallowing Frequency in Healthy Adults", *Dysphagia*, 2005, vol. 20, pp. 254-260.
Tracy, Julie F., M.A. et al., "Preliminary Observations on the Effects of Age on Oropharyngeal Deglutition", *Dysphagia*, 1989, vol. 4, pp. 90-94.
Van Willigen, J. D. et al., "On the Self-Perception of Jaw Positions in Man", *Archs oral Biol.*, 1983, vol. 28, No. 2, pp. 17-122.
Vandenbergh, Joris et al., "Regional Brain Activation During Proximal Stomach Distention in Humans: A Positron Emission Tomography Study", *American Gastroenterological Association*, 2005, vol. 128, pp. 564-573.
Woolrich, Mark W. et al., "Multilevel linear modeling for FMRI group analysis using Bayesian inference", *NeuroImage*, 2004, vol. 21, pp. 1732-1747.
Yamamoto, Takashi et al., "Taste Responses of Cortical Neurons in Freely Ingesting Rats", *Journal of Neurophysiology*, 1989, vol. 61, No. 6, pp. 1244-1258.
Yamashita, H. et al., "Magnetic sensory cortical responses evoked by tactile stimulations of the human face, oral cavity and flap reconstructions of the tongue", *Eur Arch Otorhinolaryngol*, 1999, vol. 256, pp. S42-S46.
Yoshida, Yoshikazu, MD et al., "Sensory Innervation of the Pharynx and Larynx", *The American Journal of Medicine*, 2000, vol. 108 (4A), pp. 51S-61S.

(56) References Cited

OTHER PUBLICATIONS

Yoshida, Kazuya et al., "Somatosensory evoked magnetic fields to air-puff stimulation on the soft palate", *Neuroscience Research*, 2006, vol. 55, pp. 116-122.
Zald, David H. et al., "Cortical Activation Induced by Intraoral Stimulation with Water in Humans", *Chem. Senses*, 2000, vol. 25, pp. 267-275.
Freed M. L. et al., "Electrical stimulation for swallowing disorders caused by stroke", *Respir care*, 2001, vol. 46, No. 5, p. 466.
Rosenbek, J. C. et al., "Effects of thermal application on dysphgia after stroke", *J Speech Hear Res*, 1991, vol. 34, No. 6, pp. 1257.
Lowell, Sy et al., Abstract titled "Cerebral activation patterns during swallowing and related tasks using functional magnetic resonance imaging", *Dysphagia*, vol. 22, 2007, pp. 401, 2 pgs.

\* cited by examiner

METHOD OF BRAIN ACTIVATION

This application claims the benefit of U.S. Provisional Application No. 61/006,973, filed Feb. 8, 2008, the entire disclosure of which is hereby incorporated herein by reference.

FIELD OF THE INVENTION

This invention relates to brain activation and in particular brain activation by delivery of gas or fluid pulses to a predetermined area or areas on the body.

BACKGROUND

The challenge of dealing with people who have suffered brain injury is very complex. Strokes and other trauma can cause brain injury. The literature shows that some success has been achieved in treating brain injury by manipulations that cause activation of various regions of the brain, for example by stimulating neuroplastic reorganization.

BRIEF SUMMARY

A method of activating the brain, for example by stimulating neuroplastic reorganization, is provided. In one aspect, there is provided a method of activating the brain of a subject by delivering at least one gas pulse or fluid pulse of a predetermined amplitude and duration to a predetermined area or areas on the subject's body.

In another aspect there is provided a method of rehabilitating oral sensory-motor functions by activating the regions of the cerebral hemispheres that represent the oral and oropharyngeal structures and swallowing, or by stimulating neuroplastic reorganization of the brain in the region of lateral sensory-motor cortex.

In a further aspect, there is provided a method of evaluating the effects of rehabilitation techniques that are aimed at enhancing oral sensory motor functions in terms of their effects on brain activation. For example, a method is provided for rehabilitating oral sensory motor functions that are mediated by the brain region identified as the lateral sensory-motor cerebral cortex.

In a still further aspect, there is provided a method of measuring neuroplastic reorganization of the brain in the region of the lateral sensory motor cortex.

Further features, aspects and embodiments will be described or will become apparent in the course of the following detailed description.

BRIEF DESCRIPTION OF THE DRAWINGS

The patent or application file contains at least one drawing executed in color. Copies of this patent or patent application publication with color drawings will be provided by the Office upon request and payment of the necessary fees. The invention will now be described by way of example only, with reference to the accompanying drawings, in which:

FIG. 1 shows the results of the contrast analysis. Voxels in which there was a significant difference in MR signal between the pre-SWAPT, and post-SWAPT, conditions are shown as coloured areas superimposed on an axial anatomic MR brain image. Areas that are shown in red represent voxels in which the mean MR signal was significantly greater during the pre-SWAPT condition, compared with the post-SWAPT condition. Areas shown in blue represent voxels in which the MR signal was significantly greater during the post-SWAPT condition compared with pre-SWAPT condition.

FIG. 3 shows brain activation associated with air pulsed induced swallowing. Activation was found in the bilateral pre- and postcentral gyrus, bilateral insula, anterior cingulate gyrus, and right medial frontal gyrus in response to swallows that occurred in temporal relation to air-pulse stimulation.

DETAILED DESCRIPTION OF THE DRAWINGS AND THE PRESENTLY PREFERRED EMBODIMENTS

Figure 4:
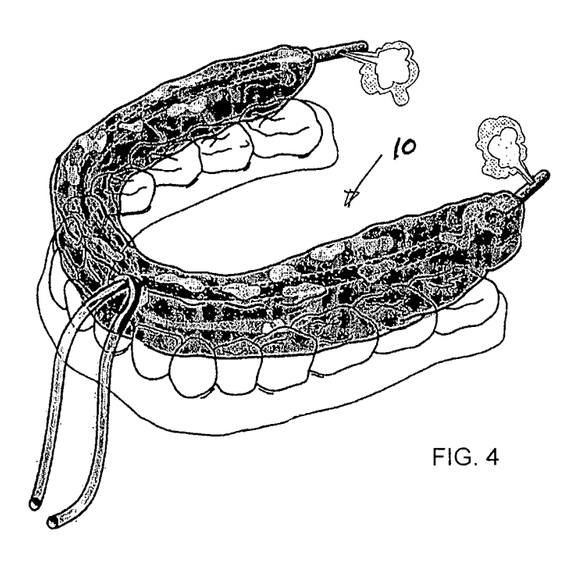
FIG. 4 is a perspective view of an oral device.

Trains of air pulses delivered to the oropharynx, either unilaterally or bilaterally, increased the frequency of saliva swallowing in healthy younger adults (Theurer et al., 2005) and older adults (Theurer et al., 2009). For example, air pulses can be delivered by way of an oral device 10 as shown in FIG. 4 and disclosed in US Patent Application Publication US 2006/0282010 A1, entitled "Oral Device," the entire disclosure of which is hereby incorporated herein by reference. Air pulses have also been used clinically to determine sensory thresholds of the laryngopharynx (Aviv et al., 1993). The air pulse has certain advantages as a somatosensory stimulus: an air pulse can be directed toward the posterior oral cavity and oropharynx, allowing examination of areas that are not accessible with other methods such as a probe. Air-pulses are natural stimuli, compared to electrical stimulation, that do not appear to evoke gustatory perceptions. In addition, air pulses activate all 4 types of cutaneous mechanoreceptors (fast adapting type 1 and 2, slowly adapting type 1 and 2) (Mizobuchi et al., 2000). Therefore, air pulses may have utility as a means of exploring the cortical representation of the oropharynx, a region believed to be critical in swallowing.

Electrophysiologic studies and brain mapping studies have provided converging evidence that cortical networks regulate autonomic and voluntary oral movements including swallowing. The tongue motor cortex, and cortical swallowing and masticatory areas, have been delineated with intracortical microstimulation. In humans, voluntary tongue movements, autonomic and voluntary swallowing, and speech movements are represented in overlapping cortical networks including pericentral, cingulate, and insular foci.

As discussed herein, a study was done to investigate the effects of oropharyngeal air-pulse trains on the activation of the brain in healthy human volunteers (Soros et al., 2008).

Experimental Procedures

The subjects were six right-handed female volunteers (mean age: 27 years, age range: 21-45 years). All subjects were non-smokers, and were not taking any medications that may have affected their oropharyngeal function. The study was conducted in accordance with the Declaration of Helsinki after approval by the University of Western Ontario Review Board for Health Sciences research involving human subjects. All individuals gave written informed consent before participating in the study.

Stimulation

Trains of air pulses were delivered to the oropharynx through a custom-made lower dental splint as previously reported (Theurer et al., 2005). There were 3, 5-min functional imaging runs. During each run, one stimulation condition was delivered: left-sided, right-sided, or bilateral oropharyngeal air-pulse stimulation. Order of stimulation was randomized. Within each run, stimuli were delivered in 6 blocks of 10 s pulse trains. Each block contained 20 air pulses (stimulation frequency: 2 Hz). Successive blocks were separated by a mean interstimulus interval (ISI) of 20 sec, with the ISI varied randomly between 15 sec and 25 sec.

Recording of Laryngeal Movements

Swallowing was identified from associated laryngeal movements that were recorded using PowerLab, v4.1.1 (ADInstruments Inc., Castle Hill, Australia) from the output signal of a pressure transducer driven from expanding MRI-compatible bellows (Siemens AG, Erlangen, Germany) positioned around the subject's neck. Participants swallowed after air pulse stimulation in the majority of trials. Swallows occurred on average 12±5.6 s (mean±standard deviation) after the onset of the stimulation.

fMRI Data Acquisition

Brain imaging was performed on a VARIAN UNITY INOVA 4 Tesla (T) whole-body MRI system (Varian Medical Systems, Inc., Palo Alto, Calif., USA) equipped with 40 mT/m Siemens Sonata actively shielded whole-body gradients and amplifiers (Siemens, Erlangen, Germany). A whole-head quadrature birdcage radio frequency (RF) coil transmitted and received the MR signal (Barberi et al., 2000). Functional data were collected from 18 contiguous, 5 mm-thick axial slices oriented approximately parallel to the anterior commissure-posterior commissure plane and extending from the superior extent of the paracentral lobule to approximately 10 mm below this plane. During each functional task described above, blood-oxygenation-level-dependent (BOLD) T2*-weighted images were acquired continuously using an interleaved, four segment, echo planar imaging sequence (64×64 matrix size, repetition time (TR)=500 ms, echo time (TE)=10 ms, flip angle=30, field of view=19.2 cm, volume collection time=2 s). Per session, 151 functional volumes were acquired (volume one was discarded). For anatomic reference, high resolution T1-weighted axial images were acquired along the same orientation as the functional images using a 3-D magnetization-prepared fast low-angle shot (FLASH) sequence (256×256×256 matrix size, 1 mm reconstructed slice thickness, TI=600 ms, TR=10 ms, TE=5.5 ms).

Data Analysis

Analysis of fMRI data was carried out in a multi-stage process using the software library FSL. An independent component analysis (ICA) was performed to detect potential imaging artifact using FSL's MELODIC (Multivariate Exploratory Linear Decomposition into Independent Components) program, an implementation for the estimation of a Probabilistic Independent Component Analysis model (Beckmann and Smith, 2004). Pre-processing of the functional data before ICA included masking of non-brain voxels, voxel-wise de-meaning of the data and normalization of the voxel-wise variance. The ICA revealed signal changes close to tissue boundaries, mainly around the edges of the brain and near the ventricles, that are typical for false positive results due to head motion. To reduce the effects of head motion in our analysis, we included the individual values for brain translation and rotation (as estimated by the previously performed motion correction) as covariates of no interest (confound explanatory variables) in the linear model for single-subject and single-condition analyses.

A univariate linear model representing the predicted hemodynamic response was fitted to the individual fMRI time series. For the first analysis, the model was based on the time course of the air-pulse stimulus trains. In the second analysis, the model was based on the time course of swallowing-related laryngeal movements that occurred following the air-pulse application. In the latter case, the time course of the air-pulse stimulation was also included in the model as a covariate of no interest. Before linear modeling, fMRI data were preprocessed including linear motion correction using MCFLIRT (Jenkinson et al., 2002), non-brain removal using BET (Smith, 2002), spatial smoothing using a Gaussian kernel of FWHM 6 mm, mean-based intensity normalization of all volumes by the same factor and high-pass temporal filtering (Gaussian-weighted least-squares straight line fitting with σ=50 s).

For a first-level analysis, the functional images of the three runs per participant (during bilateral, left, and right stimulation) were analyzed separately. Time-series statistical analysis was carried out using FILM with local autocorrelation correction (Woolrich et al., 2001). Z-statistic images were thresholded using clusters determined by Z>2.3 and a (corrected) cluster significance threshold of P=0.05. A first higher-level analysis across runs (bilateral, left, and right stimulation) for each participant individually was then carried out using a fixed effects model, by forcing the random effects variance to zero in FLAME (FMRIB's Local Analysis of Mixed Effects) [Beckmann 2003, Woolrich 2004]. A second higher-level analysis was finally performed across the combined data sets of all six participants using FLAME.

Registration to a standard brain (Montreal Neurological Institute (MNI) 152 template) was carried out using FLIRT (Jenkinson et al., 2002). Z-statistic group images were thresholded using clusters determined by Z>2.5 (air-pulse stimulation) or Z>2.3 (air-pulse-evoked swallow) and a (corrected) cluster significance threshold of P=0.05. For visualization, statistical maps were overlaid onto axial slices of the MNI 152 standard brain provided by FSL and onto a three-dimensional reconstruction of this standard brain. The reconstruction of the brain's surface was performed with FreeSurfer (Dale et al., 1999). The anatomical labels of activated brain regions were retrieved using FSLView 3.0.

Results

Saliva swallowing occurred after 91% of air-pulse stimulation blocks.

Bilateral oropharyngeal air-pulse stimulation activated the following brain regions: bilateral pre- and postcentral gyrus, the medial prefrontal gyrus, the bilateral anterior cingulate gyrus, the bilateral insula, and the right thalamus. For left-sided stimulation, activation was seen in the right and, to a lesser extent, left sensorimotor cortex. For right stimulation, activation was found primarily in the left, but also in the right sensorimotor cortex.

Figure 1:
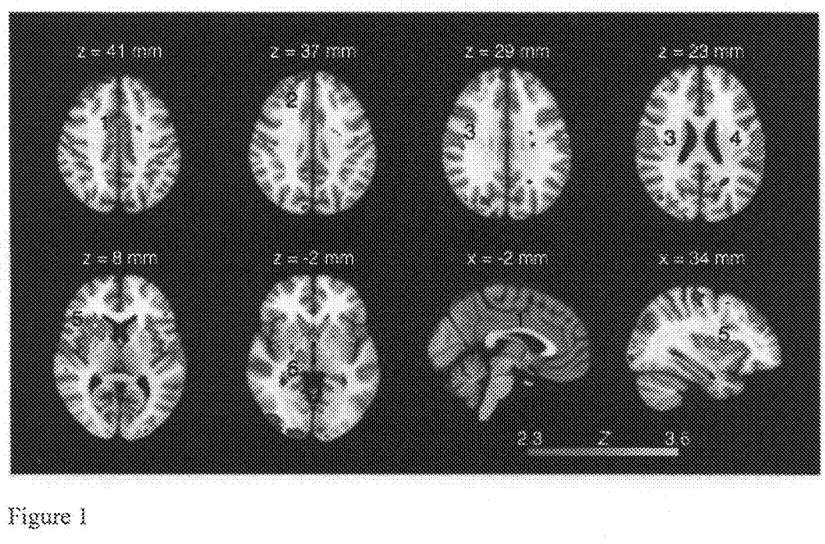
FIG. 1 shows brain activation associated with bilateral air-pulse stimulation of the oropharynx. Activation is seen in the bilateral cingulate gyrus (1), right superior frontal gyrus (2), bilateral sensorimotor cortex (3, 4), right insula (5), and right thalamus (6). Images are shown in radiological convention (the right hemisphere is seen on the left). Coordinates are given in MNI space.
Figure 2:
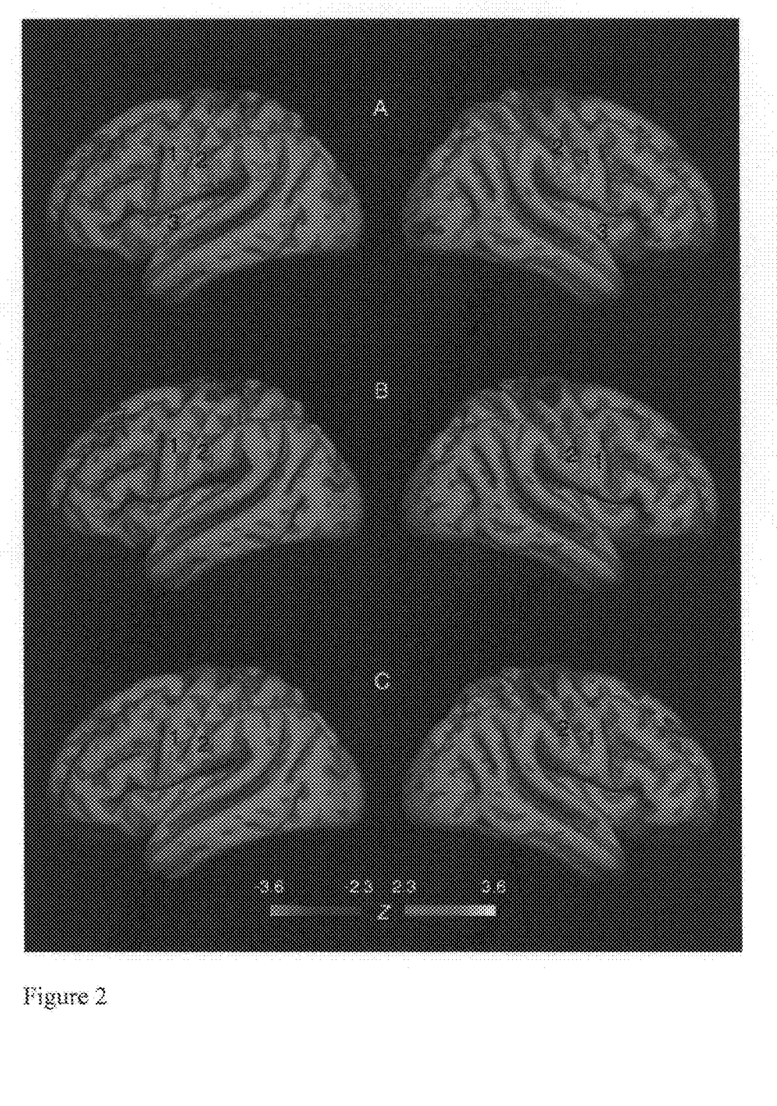
FIG. 2 shows brain activation associated with bilateral, left, and right air-pulse stimulation, overlaid onto a 3D-reconstruction of the surface of a standard brain. In the bilateral condition, activation is found in the precentral gyrus (1), postcentral gyrus (2), and insula (3).
Figure 3:
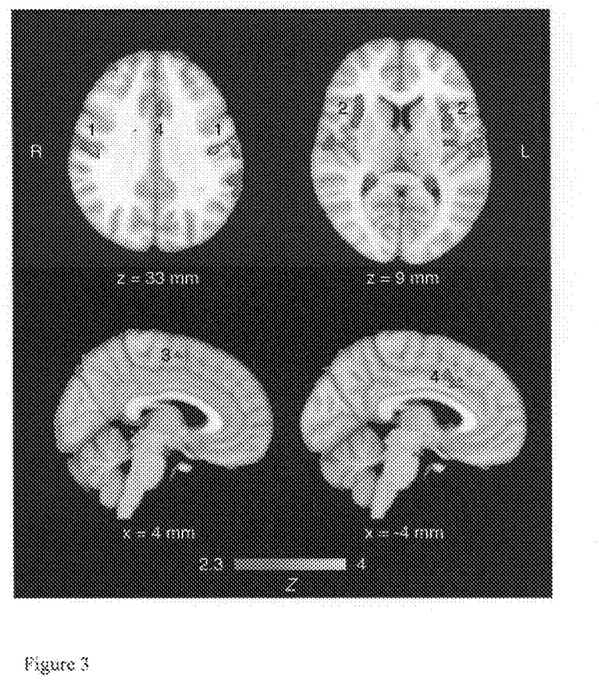

Swallows that occurred in temporal relation to air-pulse stimulation activated the bilateral pre- and postcentral gyrus, bilateral insula, anterior cingulate gyrus, and right medial frontal gyrus (see FIG. 3).

Discussion

These fMRI studies indicate that oropharyngeal stimulation with air-pulse trains activated a widely distributed network of brain areas. This network includes the somatosensory system, including the thalamus and the primary somatosensory cortex, motor areas (primary motor cortex, supplementary motor area, cingulate motor areas and basal ganglia) and polymodal regions (such as insula, inferior parietal cortex and frontal cortex). These studies also indicate that saliva swallowing that occurs in temporal relation to oropharyngeal air-pulse stimulation also activates the brain. The regions of the brain that are activated by air-pulse-related swallowing correspond to the areas that have been delineated as the cortical swallowing network in previous studies. Thus, oropharyngeal air-pulse stimulation activates the human cortical swallowing network.

Therefore, in one embodiment, a 2-week regimen of daily application of air-pulse trains to the oropharynx is associated with changes in the activation of the human brain, including the cerebral cortex and subcortical structures. This finding is consistent with the view that air-pulse application may "drive" neural reorganization, or "neuroplastic" changes.

Neural plasticity can be defined as any morphological or functional change in brain properties as a result of experience. The significance of neuroplasticity for rehabilitation is that it motivates, and provides a mechanistic rational for understanding, therapeutic interventions (Nudo et al., 2006). Evidence for neuroplasticity has come from both healthy subjects and patients with stroke, from limb and swallow/oral systems. Moreover, there is evidence that plastic change can be either adaptive or maladaptive.

The capacity to drive neuroplasticity is fundamentally important in the clinical management of patients who have suffered damage to the nervous system in that research has shown that brain injury makes the brain more sensitive to neuroplastic change. That is, central nervous system injury produces an environment in which the neuronal network is particularly receptive to modulation by specific behavioral manipulations (Nudo, 2006). Thus, the goal of neuro-rehabilitation is to exploit this heightened capacity for the injured brain to undergo reorganization by amplifying neural reorganization that is consistent with good functional outcomes, while diminishing those neuroplastic changes that are associated with poor functional outcomes, through the application of neuro-rehabilitation protocols. In relation to air-pulse application, the finding that air-pulse application is associated with changes in brain activation suggests that air-pulse application can be used to drive neuroplasticity, and associated recovery of sensorimotor function, in patients who have incurred injury to the central nervous system. This could include patients with stroke, traumatic brain injury, and cerebral palsy.

In operation, air pulse trains, of at least one pulse, ae applied to the oral cavity and oropharynx. The air pulse trains may be delivered at a pressure between 25 mmHg and 250 mmHg. Thus, the stimulus is called Swallowing Air-Pulse Therapy. Swallowing Air-Pulse Therapy is associated with changes in the functional reorganization of the brain. However, based on the current fining of change in brain activation in association with oropharyngeal air-pulse delivery, air-pulse delivery to other body parts also is likely to be associated with neuroplastic change in the regions of the brain mediating function of those body parts. For example, air-pulse delivery to the face would be expected to be associated with altered neural processing of facial sensorimotor function, based on our current findings described below.

A number of factors have been shown to drive neural plasticity. These include motor skill acquisition, injury, transcranial magnetic stimulation and electrical stimulation, and sensory manipulations.

Studies of limb motor skill acquisition in healthy subject and patients with stroke have shown that motor learning is critical for neuroplasticity. Motor training leads to expansion of motor representation of the trained hand. These findings have been applied in rehabilitation therapies, for example, Constraint-Induced Therapy. In Constraint-Induced Therapy, following a brain lesion such as stroke, training the affected hand (the hand that is paretic (weak) after stroke) while limiting use of the unaffected (stronger) hand expands the hand representation of the affected hand into the neighboring elbow and shoulder representations, and is associated with improved performance.

The oropharyngeal system may show patterns of neural plasticity that are distinct from the limb system for several reasons. Unlike the limbs, oral and pharyngeal movements involve coactivation of paired muscles that are organized about the body midline. There are significant contralateral and ipsilateral corticobulbar components in the oral system. Muscles within the oral system, such as those in the tongue, are highly specialized. Finally, the oral and oropharyngeal systems give rise to both voluntary (e.g., speech) and autonomic (automatic) (e.g., swallowing) sensorimotor functions Evidence that neuroplasticity can occur with the oropharyngeal system has come from both animal and human studies. Intracortical microstimulation effects and neuronal activity patterns provided evidence that a tongue task training drives plastic changes within primate face primary motor cortex (Sessle, 2006). It is important to recognize that the tongue task, that involves the monkey pressing its tongue against a force transducer positioned immediately in front of monkey's face, involves not only movement generation but also sensory stimulation of the tongue as it contacts the force transducer and controls the force or applied tongue protrusion. Thus, the associated neuroplastic changes could be related to motor and sensory mechanisms. In humans, a similar tongue protrusion task performed for several days has been associated with changes in the topography and excitability of the tongue motor cortex (Svensson et al., 2003; 2006.

There is also evidence that various neuroplastic changes occur within distinct time periods, with some changes being rapid and other being slow. Thus, some authors have proposed two steps of plasticity (Pascual-Leone). The unmasking of existing brain connections is seen as a competitive and rapid process. This is in contrast to the slower neuroplastic process of establishing new neural connections. New neural connections may be local to the site of nervous system damage, or in areas remote from the injury.

Mutual interhemispheric inhibition has been shown to play a role in neuroplastic change after brain injury. Recovery of limb motor function and language after stroke are associated with activation shift toward the damaged hemisphere. However, for tongue movements, the unaffected hemisphere appears to be responsible for recovery from unilateral lingual paralysis following unilateral hemispheric stroke, likely by potentiating the effect of preexisting ipsilateral pathways (Muellbacher et al., 1999). Swallowing recovery post-stroke is associated with expansion of pharyngeal motor cortical representation in the unaffected hemisphere (Hamdy et al., 1998)

With regards to stimulation that drives neuroplastic change, reduced sensory input, or low frequency transcranial magnetic stimulation, to the unaffected sensorimotor cortex is associated with gain in limb motor function in healthy controls and in patients with chronic stroke. For swallowing, in patients with dysphagia following stroke, pharyngeal electrical stimulation is associated with increased swallowing corticobulbar excitability mainly in the unaffected hemisphere; this is correlated with improvement in swallowing function (Fraser et al., 2002).

There is some evidence that sensory stimuli can modulate swallowing. Stimuli that have been examined to date include Thermal-Tactile application (Rosenbek et al.), and bolus properties such as temperature, taste, and consistency. Recently, Theurer et al. (2005) showed that air pulses trains delivered to the oropharynx increase the frequency of saliva swallowing in healthy controls. To date, the effects of these sensory applications on brain function have not been reported.

Sensory Physiology of Swallowing

The pharyngeal stage of swallowing, which affords both airway protection and bolus transport, is evoked when an appropriate pattern of sensory input excites multimodal neurons of the nucleus tractus solitarius and adjacent reticular formation within the dorsal medulla. Stimulation of receptive fields innervated by the superior laryngeal nerve (SLN) and the pharyngeal branch of the glossopharyngeal nerve (GPNph) are particularly effective in evoking the pharyngeal swallow. These "reflexogenic" areas correspond to the laryngeal mucosa, including the epiglottis and arytenoids (i.e., innervated by the SLN), and the lateral pharyngeal wall, posterior tonsillar pillar and peritonsillar areas (i.e., innervated by the GPNph).

In humans, although the anterior faucial pillar was historically been considered the most reflexogenic site for swallowing, the finding that the pharyngeal swallow begins after the bolus head passes the anterior faucial pillars suggests that stimulation of more posterior pharyngeal regions is required to elicit swallowing. Consistent with this, the human posterior tonsillar pillar, as well as discrete regions of the palate, pharynx and epiglottis are innervated by a dense plexus formed from the GPNph and the internal branch of the SLN. The close correspondence between these areas of dual innervation and reflexogenic areas for swallowing has lead to the hypothesis that swallowing is elicited most readily by stimulation of areas innervated by both the GPNph and SLN. In addition, it appears that dynamic stimuli that excite primary afferents within a number of receptive fields, most readily elicit swallowing.

It is important to recognize that peripherally evoked swallowing can be modulated by descending cortical and subcortical inputs. In animal models, swallowing evoked by electrical stimulation of the SLN is facilitated by simultaneous electrical stimulation of specific cortical regions. In humans, transcranial magnetic stimulation of the lateral motor cortex increases the amplitude of electromyographic (EMG) activity associated with swallowing. Consistent with this, the clinical literature suggests that delayed triggering of the pharyngeal swallow is the most common swallowing abnormality in supratentorial stroke, ranging from mild to severe depending on lesion location and single versus multiple strokes. Thus, cortical dysfunction may increase the threshold for peripherally evoked swallowing, perhaps through altered corticofugal inputs to the brainstem swallowing network.

Oropharyngeal Sensory Deficits in Hemispheric Stroke

Although dysphagia in hemispheric stroke traditionally has been attributed to motor impairment, recent studies have documented frank sensory deficits in dysphagic stroke patients and suggested a causal link between sensory impairment, aspiration, and aspiration pneumonia. As discussed above, the observation that delayed triggering of the pharyngeal stage is the most common swallowing abnormality in supratentorial stroke is itself indirect evidence of a sensory deficit. Moreover, a series of studies by Aviv have shown that, whereas healthy subjects are able to detect trains of discrete air pulses delivered endoscopically to the mucosa of the pyriform sinus and aryepiglottic fold (i.e., both innervated by the SLN) at pressures below 4.0 mmHg (with no right-left or gender differences), sensory thresholds for dysphagic stroke subjects were elevated beyond 6.0 mm Hg. This was true whether the sensory thresholds were determined based on psychophysical testing or from elicitation of the laryngeal adduction reflex. Sensory detection thresholds increased with age (i.e., over 60 years of age), underscoring the need for an age-matched control group in sensory studies of dysphagia in stroke. Importantly, Aviv has also reported that aspiration was more common in dysphagic stroke patients who showed laryngopharyngeal sensory deficits, especially if the sensory deficit was bilateral. Furthermore, the false-negative rate (FNR) for aspiration pneumonia associated with the Modified Barium Swallow (MBS; a "gold-standard" fluoroscopic swallowing examination using barium contrast) is substantially higher than that associated with MBS plus laryngopharyngeal sensory testing. The sensory testing identified a subgroup of patients who develop aspiration pneumonia, did not show frank aspiration on the MBS and had bilateral LP sensory deficits. In agreement with these findings, reduced pharyngeal sensation (i.e., tested manually with a blunt wooden probe) was 1 of 3 factors significantly associated with aspiration on MBS, independent of stroke severity. This is consistent with a meta-analysis showing that screening for impaired laryngopharyngeal sensation was 1 of only 2 screening methods accurate in detecting aspiration as a marker of dysphagia.

Oropharyngeal Sensitisation Therapies

A number of investigators have advocated increasing oropharyngeal sensory input as a means of facilitating swallowing. Sensory stimulation has been manipulated by changing properties of the bolus (e.g., sour bolus, chilled bolus), and by direct mechanical or thermomechanical stimulation applied to the anterior tonsillar pillars. These approaches have achieved widespread clinical acceptance in spite of the fact their efficacy has not been established. For example, while some authors have reported that cold mechanical stimulation of the anterior tonsillar pillar decreases swallowing latency and increases swallowing frequency, others have failed to find an effect of this type of stimulation on oropharyngeal bolus transit, esophageal coordination, or the temporal pattern of swallowing. Similarly, whereas some authors have reported that swallowing latency is significantly reduced by a combination of mechanical, cold, and gustatory (sour) stimulation, others have reported that a cold+sour bolus slowed swallowing. Logemann has suggested that a sour bolus facilitates swallowing in stroke.

Three studies have examined the effects of cold mechanical stimulation applied to the anterior tonsillar pillars on swallowing in small samples of dysphagic stroke patients. They reported a short-term facilitation of swallowing, measured in terms of reduced delay of the pharyngeal swallow, in some patients, with no related reduction in aspiration. Longitudinal studies, examining the potential long-term effects of oropharyngeal sensitisation, have not been reported; this is a serious shortcoming in the swallowing rehabilitation literature.

Cerebral Cortical Mechanisms of Swallowing in Health and in Stroke

Brain-imaging studies in healthy subjects conducted by ourselves and others have shown that voluntary, as well as "autonomic", swallowing activates a large interhemispheric network of cortical and subcortical regions. The most prominent activation focus corresponds to the lateral postcentral gyrus and parietal operculum (i.e., primary and secondary somatosensory cortex), underscoring the importance of sensory processing in swallowing regulation. Other prominent areas of activation correspond to the lateral precentral gyrus, perisylvian cortex, insula, and anterior cingulate cortex. The finding of swallow-related activation within the lateral pericentral and perisylvian areas is in keeping with electrophysiologic studies of swallowing and related oral functions. For example, we demonstrated that intracortical microstimulation (ICMS) applied to four cortical regions evokes swallowing in awake primates: the face primary somatosensory cortex (face-SI), face primary motor cortex (face-MI), Brodmann's area (BA) 6 immediately lateral to face-MI, and the inner wall of the frontal operculum. The finding that swallowing was evoked from SI, as well as MI, again highlights the role of sensory mechanisms in swallowing control. Changes in stimulus intensity altered the amplitude and latency of swallow-related (EMG) activity, suggesting that the pericentral cortex plays a role in both swallowing modulation and initiation. Consistent with these ICMS findings, we documented "swallow-related" neurons in face-MI and the more lateral BA 6. Our brain-imaging studies have also shown that swallow-related activation of the lateral postcentral gyrus and parietal operculum is strongly lateralized to the left hemisphere in the majority of subjects, independent of handedness. In contrast, insular processing of swallowing appears to be lateralized to the right hemisphere. We also have reported that older adults show similar patterns of brain activation in association with swallowing to those of young subjects, with the exception of overactivation of the right pericentral, premotor cortex for water swallowing only.

Our fMRI studies in patients have shown that the cortical representation of swallowing is abnormal following hemispheric stroke. For voluntary swallowing of saliva, activation of the precentral and postcentral gyri are significantly reduced ($p<0.05$), relative to that seen in healthy age-matched controls, and there appears to be overactivation within other regions of the contralesional hemisphere. These brain-imaging findings are supported by studies in primates showing that bilateral cold block of the ICMS-defined "swallowing cortex" decreases the frequency and alters the EMG profile of swallowing. Although few human studies have been reported, one previous study showed that dysphagic patients showed a smaller TMS-defined pharyngeal motor cortex representation in the contralesional hemisphere, compared with non-dysphagic controls a finding that was interpreted as suggesting that dysphagia occurred because of damage to the "swallow dominant" hemisphere. Swallowing recovery was associated with an expansion of the pharyngeal motor cortex representation within the contralesional hemisphere, suggesting that reorganization of the intact motor cortex was driving swallowing recovery.

Abnormal patterns of brain activation following stroke also have been reported for language tasks and motor tasks performed with the affected hand. These abnormal patterns, which arise early after stroke, include increased bilateral activation, recruitment of additional sensory and secondary motor cortical areas, expansion of the hand sensorimotor representation into the face area, and peri-infarct activation. Furthermore, longitudinal studies have shown that over-recruitment lessens over time, with activation shifting toward the sensorimotor cortex of the lesioned hemisphere and the peri-infarct region. While the associations between these patterns of brain activation and clinical recovery are less clear, a small number of studies have suggested that return of sensorimotor processing to the lesioned hemisphere is associated with superior recovery.

Persistent functional changes within the sensorimotor cortex can be induced not only as a result of stroke but also following transient manipulation of sensory input or motor output. In a series of classis primate studies, Merzenich and colleagues have shown that cortical sensory and motor representations are dynamic structures, changing over the lifespan as a function of experience. This evidence has clear implications for rehabilitation, fuelling the view that sensory and motor manipulations can drive functional recovery possibly by facilitating the return of processing within pre-stroke neural networks. To date, a small number of intervention studies have addressed this issue with respect to limb movement and provided some evidence that motor intervention is associated with cortical reorganization toward pre-stroke networks.

Three studies have addressed plastic brain changes induced by manipulations within the oral sensorimotor system. Svensson et al. recently reported that tongue motor training was associated with an increase in the size of the TMS-defined tongue motor cortex representation in healthy adults. More germane to swallowing, Hamdy et al., showed that a 10-min period of electrical stimulation applied to the pharynx of healthy adults increased (i) the size of the TMS-defined pharyngeal motor cortex representation and the amplitude of TMS-evoked pharyngeal EMG activity for up to 30 minutes, and (ii) the fMRI-defined sensorimotor activation associated with water swallowing. In stroke subjects, electrical pharyngeal stimulation increased the amplitude of TMS-evoked pharyngeal EMG responses; these increases were associated with aspiration during swallowing pre- and post-stimulation. These findings highlight the potential for functional brain reorganization and associated swallowing recovery following stroke.

Experimental Procedures

Experiment 1: Changes in Brain Activation Following a Period of SWAPT

Participants

Four female and one male volunteers with no history of swallowing, orofacial, gastrointestinal, respiratory, or neurological problems participated in the study (mean age: 27 years, age range: 21-45 years). The study was conducted in accordance with the Declaration of Helsinki after approval by the University of Western Ontario Review Board for Health Sciences research involving human subjects. All individuals gave written informed consent before participating in the study.

Experimental Design

Each subject participated in one brain-imaging experiment before, and one brain-imaging experiment after, a 14-day regimen of SWAPT. During the 14-day regimen, each subject received SWAPT twice daily, for 20 minutes during each daily session. During each daily session, air-pulses were 10 sec trains, 2 Hz, interstimulus interval 20 sec.

Delivery of Air-Pulse Stimulation

For oropharyngeal stimulation, trains of air pulses were delivered through a custom-made lower dental splint. A lower dental impression was used to make a cast of the individuals' mouth. The splint was created by vacuum forming bleaching material (5" by 5", 0.04 EVA) over the dental cast. Fine polyethylene tubing (inner diameter;

0.045"; outer diameter 0.062") is then secured to the splint along the gingival contours of the dental cast. A second layer of bleaching material is then vacuum-formed over the first layer, enclosing the polyethylene tubing. Air pulses were delivered to the oropharynx through the polyethylene tubing housed within the oral splint. The air pulses were generated by connected tubing to a manually-controlled sphygmomanometer. Movement signals will be digitized on-line using Powerlab v2.0 (ADInstruments). Stimulation was performed in response to a visual cue that was projected on a screen inside the magnet room, visible to the experimenter but not to the participant.

SWAPT FMRI Task Conditions

The fMRI sessions that were conducted before, and after, the 14-day SWAPT regimen were identical in terms of experimental protocol: Each subject participated in six, 7-min functional imaging runs during a single experimental session. During the first imaging run, the subject voluntarily swallowed her accumulated saliva once every 40 seconds without producing exaggerated oral movements. During the following two runs, bilateral air pulse trains of either 10 sec or 1 sec duration were administered. The interval between the onset of air pulse trains was pseudo-randomized (25-35 s). Subsequent to these imaging runs was a 10 minute, no imaging, period of 10 minutes where the subject received 10 sec air pulse trains with an inter-stimulus interval of 25-35 seconds. The initial three functional imaging runs were then repeated after the treatment period. The order of these runs was randomized across individuals.

Recording of Laryngeal and Respiratory Movements

Laryngeal and respiratory movements were recorded using PowerLab, v4.1.1 (ADInstruments, Castle Hill, Australia) from the output signal of a pressure transducer driven from expanding MRI-compatible bellows (Siemens, Erlangen, Germany) positioned comfortably over the subject's thyroid cartilage and ribcage respectively, as been reported previously (Martin et al., 2001). In the vast majority of events, participants swallowed after air pulse stimulation. Swallows occurred on average 12 sec after the onset of the stimulation.

fMRI Data Acquisition

During both the pre-SWAPT, and post-SWAPT fMRI sessions, brain imaging was performed on a Varian UNITY INOVA 4 Tesla (T) whole-body MRI system (Varian, Palo Alto, Calif., USA) equipped with 40 mT/m Siemens Sonata actively shielded whole-body gradients and amplifiers (Siemens, Erlangen, Germany). A whole-head quadrature birdcage radio frequency (RF) coil transmitted and received the MR signal (Barberi et al., 2000). The subject's head was restrained with foam padding. Functional data were collected from 18 contiguous, 5 mm-thick axial slices oriented approximately parallel to the anterior commissure-posterior commissure plane and extending from the superior extent of the paracentral lobule to approximately 10 mm below this plane. During each functional task described above, blood-oxygenation-level-dependent (BOLD) T2*-weighted images were acquired continuously using an interleaved, four segment, echo planar imaging sequence (64×64 matrix size, repetition time (TR)=500 ms, echo time (TE)=10 ms, flip angle=30, field of view=19.2 cm, volume collection time=2 s). Each image was corrected for physiologic fluctuations using a navigator echo that was collected at the beginning of every image segment (Hu and Kim, 1994). Per session, 151 functional volumes were acquired (volume one was discarded). To remove the fraction of the BOLD signal that arises from cerebral and pial vessels, a motion-suppression algorithm developed by Menon was applied to the data (Menon, 2002; Martin et al., 2007). For anatomic reference, high resolution T1-weighted axial images were acquired along the same orientation as the functional images using a 3-D magnetization-prepared fast low-angle shot (FLASH) sequence (256×256×256 matrix size, 1 mm reconstructed slice thickness, TI=600 ms, TR=10 ms, TE=5.5 ms).

Data Analysis

All images were performed using Brain Voyager v4.9 (Brain Innovation, Maastricht, Netherlands) (Goelbel 2001). Two-dimensional (2D) functional slices were coregistered with the 3D anatomic images to generate volume-time courses. The anatomic images were aligned with the AC-PC plane and transformed to standard stereotaxic space (Talairach and Tournoux 1988). The data were spatially smoothed with a Gaussian filter (full width at half maximum=4 mm) to facilitate group analyses.

Brain activation associated with performance of the activation tasks was identified using multiple regression analysis. Predictors were generated by convolving a square-wave function representing the time course of the experimental tasks with a γ function (γ=2.5; τ=1.25) representing the hemodynamic impulse response (Boynton et al. 1996; Cohen 1997). The square wave function was constructed by assigning a value of 1 to the imaging volumes during which the triggers for the visual cues were delivered, and 0 to all other imaging volumes. Voxel-wise statistical contrast analyses were performed to determine voxels in which there was a significant difference in the mean amplitude of the MR signal during the Pre-SWAPT and post-SWAPT fMRI conditions.

TABLE 1

Results of contrast analysis showing voxels in which the mean MR signal was significantly greater (blue), or less (red) during the post-SWAPT condition compared to the pre-SWAPT condition. Prominent regions in which brain activation was significantly greater following the 14-day regimen of SWAPT were localized to the left (lateral) sensorimotor cortex, right sensorimotor cortex, insula, and left parietal lobe.
14 day single pre vs post individual contrast
P(cor) 0.000696
Cl 4.2-8
Talairach Coordinates

| 18 | −12 | 38  | 128 |
| 20 | −40 | 31  | 207 |
| 23 | 30  | −37 | 208 |
| 24 | 6   | 58  | 165 |
| 25 | −26 | 32  | 328 |
| 26 | −42 | −58 | 81  |
| 27 | −16 | −58 | 271 |
| 29 | −12 | −45 | 218 |
| 30 | 3   | 44  | 35  |

Generally speaking, the systems described herein are directed to brain stimulation. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to brain stimulation.

As used herein, the terms "comprises" and "comprising" are to construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

The invention claimed is:

1. A method of activating the brain of a subject comprising:
   delivering a train of fluid air pulses of a predetermined frequency and duration at a pressure between 25 mmHg and 250 mmHg with an oral device to one or more predetermined areas on the subject's body selected from the group consisting of a peri-tonsillar area, tongue, mouth, oral cavity, oropharynx, nasal cavities, pharynx and neck of the subject;
   eliciting swallowing by the subject in response to the delivering of the train of fluid air pulses; and
   activating a brain of the subject directly in response to the delivering of the train of fluid air pulses, or the swallowing that was elicited in response to the delivery of the train of fluid air pulses.

2. A method of activating the brain as claimed in claim 1 wherein the delivering the train of fluid air pulses comprises delivering the train of fluid air pulses for a predetermined period of time.

3. A method of activating the brain as claimed in claim 2 wherein the delivering the train of fluid air pulses for the predetermined period of time is a session and further including delivering a predetermined number of sessions.

4. A method of activating the brain as claimed in claim 2 wherein the predetermined period of time has a duration of less than or equal to 20 seconds.

5. A method of activating the brain as claimed in claim 1 wherein the predetermined frequency is between 0.5 and 30 Hertz.

6. A method of activating the brain as claimed in claim 1 wherein the delivering the train of fluid air pulses is used for one or more of testing purposes, diagnosing purposes, monitoring purposes and therapeutic purposes.

7. A method of rehabilitating oral sensory motor functions by activating the brain according to the method of claim 1.

8. A method of rehabilitating oral sensory motor functions as claimed in claim 7 wherein the oral sensory motor function is selected from the group consisting of swallowing, salivating, masticating, speech, and producing reflexive and/or voluntary oral movements or oropharyngeal movements or laryngeal movements.

9. The method of claim 1 wherein the oral device comprises a dental splint.

* * * * *